US00PP36852P2

(12) United States Plant Patent
van Noort

(10) Patent No.: US PP36,852 P2
(45) Date of Patent: Jul. 22, 2025

(54) ***GERANIUM* PLANT NAMED 'MVNG1901'**

(50) Latin Name: *Geranium sanguineum*
Varietal Denomination: MVNG1901

(71) Applicant: Marco van Noort, Warmond (NL)

(72) Inventor: Marco van Noort, Warmond (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 19/048,919

(22) Filed: Feb. 8, 2025

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./263.1, 324
See application file for complete search history.

(56) References Cited

U.S. PATENT DOCUMENTS

PP34,576 P2 * 9/2022 Lubbe ..... Plt./324

* cited by examiner

*Primary Examiner* — Karen M Redden
(74) *Attorney, Agent, or Firm* — Penny J. Aguirre

(57) ABSTRACT

A new cultivar of *Geranium sanguineum* plant named 'MVNG1901' that is characterized by its flowers that are relatively large in size and violet-pink in color, its floriferious blooming habit, its re-blooming habit throughout the season, its flowering season that commences early in the season, and its compact and spreading plant habit.

2 Drawing Sheets

Botanical classification: *Geranium sanguineum.*
Cultivar designation: 'MVNG1901'.

CROSS-REFERENCE TO RELATED APPLICATIONS

This application is related to a European plant breeders' rights application filed on Sep. 1, 2023, application No. 2023/1836. The Information for the Plant Breeders' Rights Application was received directly from the Inventor. This application is also co-pending with a U.S. Plant Patent Applications filed for plants derived from the same breeding program that are entitled *Geranium* Plant Named 'MVNG1811' (U.S. Plant patent application Ser. No. 19/048,917) and *Geranium* Plant Named 'MVNG1905' (U.S. Plant patent application Ser. No. 19/048,920).

BACKGROUND OF THE INVENTION

The present invention relates to a new and distinct cultivar of *Geranium* plant, botanically known as *Geranium sanguineum* 'MVNG1901' and will be referred to hereafter by its cultivar name, 'MVNG1901'. 'MVNG1901' is a new cultivar of herbaceous perennial grown for use as a garden plant.

'MVNG1901' arose from an on going breeding program conducted by the Inventor in Warmond, The Netherlands. The objectives of the breeding program is to develop new cultivars of *Geranium* that have healthy growth habits, re-blooming habits, and resistance to higher temperatures in dryer locations.

'MVNG1901' originated as a seedling that arose from seed planted from open pollination of *Geranium sanguineum* 'Canon Miles' (not patented) in May of 2020. The male parent is therefore unknown. 'MVNG1901' was selected as a single unique plant in June of 2021 from the resulting seedlings.

Asexual propagation of the new cultivar was first accomplished by stem cuttings under the direction of the Inventor in Warmond, The Netherlands in December of 2023. Asexual propagation by stem cuttings and tissue culture tissue culture using meristematic tissue has determined that the characteristics of the new cultivar are stable and are reproduced true to type in successive generations.

SUMMARY OF THE INVENTION

The following traits have been repeatedly observed and represent the characteristics of 'MVNG1901'. These attributes in combination distinguish 'MVNG1901' as a new and distinct cultivar of *Geranium.*

1. 'MVNG1901' exhibits flowers that are relatively large in size and violet-pink in color.
2. 'MVNG1901' exhibits a floriferious blooming habit.
3. 'MVNG1901' exhibits re-blooming throughout the season.
4. 'MVNG1901' exhibits a flowering season that commences early in the season.
5. 'MVNG1901' exhibits a compact and spreading plant habit.

The female parent of 'MVNG1901' is similar to 'MVNG1901' in having flowers that are similar in color. The female parent of 'MVNG1901' differs from 'MVNG1901' in having flowers that are smaller in size, a blooming season that commenses later in the season, and a less compact and less dense plant habit. 'MVNG1901' can be most closely compared to the *Geranium* cultivar 'Glenluce' (not patented). 'Glenluce' is similar to 'MVNG1901' in foliage characteristics. 'Glenluce' differs from 'MVNG1901' in having a blooming season that commenses earlier in the season, a shorter plant height, and flowers that are smaller and more rounded in form with less space between the flower petals.

'MVNG1901' can also be compared to the co-pending cultivars of *Geranium*; 'MVNG1811' and 'MVNG1905'. 'MVNG1811' differs from 'MVNG1901' in having light pink flowers. 'MVNG1905' differs from 'MVNG1901' in having flowers that open pink in color and change to violet-purple in color.

BRIEF DESCRIPTION OF THE DRAWINGS

The accompanying color photographs illustrate the overall appearance and distinct characteristics of the new *Geranium*. The photographs were taken of one year-old plants of 'MVNG1901' as grown in a 19-cm circular container outdoors in Warmond, The Netherlands.

The photograph in FIG. 1 provides a top view of 'MVNG1901' in bloom.

Figure 1:
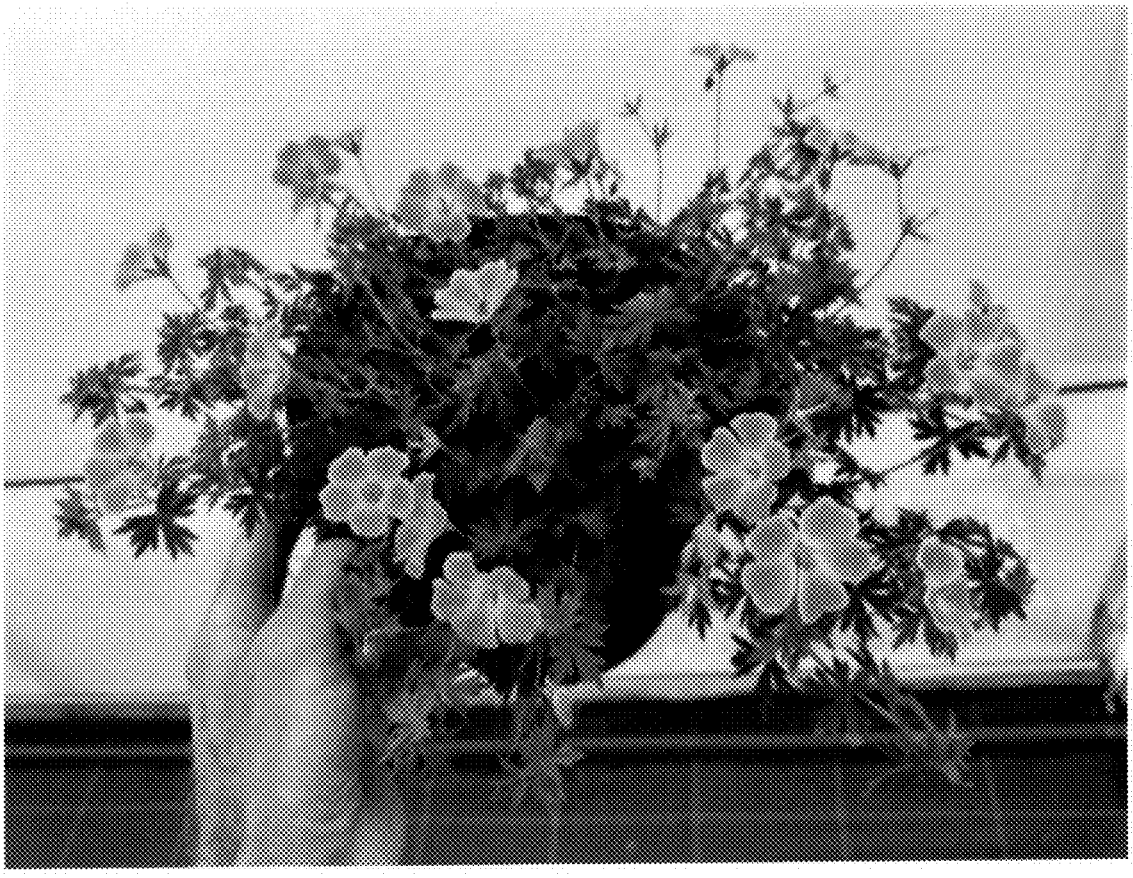
Figure 2:
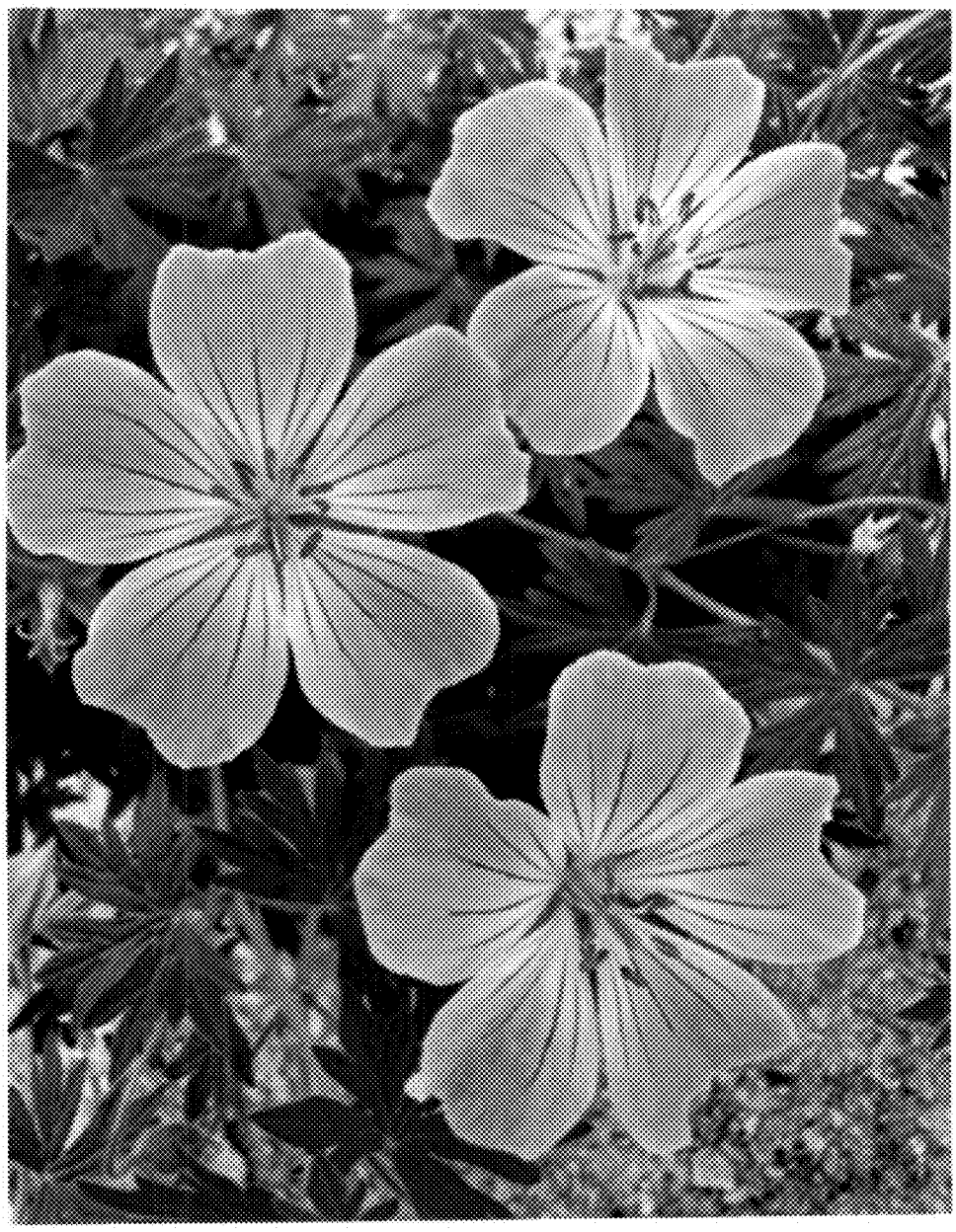

The photograph in FIG. 2 provides a close-up view of the flowers of 'MVNG1901'.

The colors in the photographs are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one year-old plants of the new cultivar as grown outdoors in a 19-cm container in Warmond, The Netherlands. The phenotype of the new cultivar may vary with variations in environmental, climatic, and cultural conditions, as it has not been tested under all possible environmental conditions. The color determination is in accordance with the 2015 $6^{th}$ edition Colour Chart of The Royal Horticultural Society, London, England, except where general color terms of ordinary dictionary significance are used.

General characteristics:

*Blooming period*.—Spring into late summer in The Netherlands.

*Plant type*.—Herbaceous perennial.

*Plant habit*.—Flattened, broadly spreading, compact.

*Height and spread*.—Average of 19.7 cm in height and 37 cm in spread as a one year-old plant as grown in a container.

*Hardiness*.—At least in U.S.D.A. Zones 5 to 9.

*Diseases and pests*.—No susceptiblity or resistance to disease or pests has been observed.

*Root description*.—Slightly fleshy, overall average diameter of the root system is 2 mm, both shallow and moderately deep distribution into the soil, moderate density, moderately branched, smooth and glabrous surfaces, 164C in color.

*Root development*.—Average of 6 to 8 weeks for root initiation, 12 to 14 weeks to produce a rooted cutting.

*Growth rate*.—Moderately vigorous.

*Growth habit*.—Strong.

*Propagation*.—Stem cuttings and tissue culture.

Branch description:

*Branch size*.—Average of 20.5 cm in length and 2 mm in width.

*Branch shape*.—Round.

*Branch strength*.—Moderately strong.

*Branch aspect*.—Average of 40°.

*Branch color*.—Young; 144A, mature; 144A to 144B.

*Branch surface*.—Slightly glossy and moderately covered with short hairs, average of 1 mm in length and too small to measure color.

*Internode length*.—Average of 4.5 cm.

*Branching habit*.—Freely branched, average of 34 main branches, 34 lateral branches.

Foliage description:

*Leaf shape*.—Reniform (overall shape), palmately cleft with an average of 5 lobes.

*Leaf division*.—Simple.

*Leaf base*.—Hastate, lobes free.

*Leaf apex*.—Acute.

*Leaf venation*.—Palmate, upper surface 144A, lower surface 146C.

*Leaf margins*.—Lanciniate.

*Leaf lobes*.—Sinuses are deep, sinus orientation is divergent.

*Leaf attachment*.—Petiolate.

*Leaf arrangement*.—Opposite.

*Leaf surface*.—Both surfaces non-rugose, upper surface very slightly glossy, lower surface slightly glossy, covered with short hairs; an average of 0.5 mm in length, N155A in color.

*Leaf color*.—Young upper surface; 144A, young lower surface; 143C, mature upper surface; NN137C, mature lower surface; NN137C.

*Leaf size*.—Average of 3.2 cm in length and 3.5 cm in width.

*Leaf quantity*.—Average of 10 (5 pairs) per lateral branch.

*Petioles*.—Average of 2.3 cm in length and 1 mm in width, upper and lower surface color 144A, both surfaces are slightly glossy, densely covered with short hairs an average of 1.25 mm in length and N155A in color, high strength.

*Stipules*.—2 leafy stipules, present at the base of the leaves, narrow deltoid in shape, apex is cillate, broad cuneate base, an average of 3 mm in length, 1.5 mm in width, N167A in color, margin sparsely covered with short hairs; 0.5 mm in length and too small and sparse to measure color.

Flower description:

*Inflorescence type*.—Axillary, solitary.

*Lastingness of flowers*.—Average of 7 days, self cleaning.

*Flowers*.—Up to 34 per plant, rotate, single, average of 3.5 cm and diameter, 1.5 cm in depth, primarily upward to outward facing.

*Flower fragrance*.—None.

*Flower bud*.—Up to 140 per plant, an average of 9 mm in length, 5 mm in width, color; 138B, veined 138B, elliptic in shape, surface is densely covered with short glandular hairs an average of 0.75 mm in length, color; 138A, axially striped 138B.

*Petals*.—5, rotate in arrangement, 1 whorl, obcordate in shape, narrow cuneate base, broadly retuse apex, entire margins, surfaces are glabrous, velvety, and matte, average of 2 cm in length, 1.7 cm in width, color: when opening upper surface; N80B to N80C, base a blend of N75D and N80D, veins N81A, when opening lower surface; N80D, base N80D, veins N81A, when fully open upper surface; N78C, base; 76A, veins N81A, fading after maturity to N75B, base 76B, veins N81A, when fully open lower surface; 76A, tinged slightly darker at the top; N78D, veins N81A, changing after maturity to 76A, base 76C, veins N81A.

*Calyx*.—Rotate, average of 5 mm in length and 1.8 cm in width.

*Sepals*.—Average of 5, broadly ovate in shape, entire margins, mucronate apex, cuneate base, average of 1 cm length, 4.5 mm in width, upper surface glabrous, smooth, moderately glossy, lower surface glabrous, smooth, matte and densely covered with short hairs 0.75 mm in length, a blend of N155A and 156D in color, color: when opening upper surface; 138B, axially veined 138A, margins transparent 157D, when opening lower surface; 138B, axially veined 137B, margins transparent 157D, when fully open upper and lower surface; 144A, margins 157D, veins 137A and 137B, non-fading.

*Peduncles*.—Average of 8.1 cm in length and 1 mm in diameter, moderately to strong, held in a 35° angle to lateral branch, 144A to 144B in color, surfaces are slightly glossy and densely covered with short hairs; average of 0.75 mm in length and NN155D in color.

*Pedicels*.—None.

*Floral bracts*.—Two bracts are placed at the top of about half of the flowers, lanceolate in shape, average of 3 mm in length, 1.5 mm in width, entire margins, narrow acuminate apex, cuneate base, upper surface smooth and glabrous, margins densely covered with short hairs; average of 0.5 mm in length, NN155D in color, both surfaces N167A in color.

Reproductive organs:

*Gynoecium*.—Pistil; 1, average of 6 mm in length, stigmas; 5, curled, 2.5 mm in length, 6 mm in diameter, 171D in color, style; average of 3.5 mm in length, color; N170B, ovary is 143B in color.

*Androecium*.—Stamens; 10, anthers; narrow oblong in shape, 2 mm in length, 0.75 mm in width, N77C in color, filaments; 8 mm in length, 73D in color, pollen is moderate in quantity and 79B in color.

*Fruit/seeds*.—None observed to date.

It is claimed:

1. A new and distinct cultivar of *Geranium* plant named 'MVNG1901' as herein illustrated and described.

* * * * *